United States Patent [19]

Nesvadba et al.

[11] 4,020,166
[45] Apr. 26, 1977

[54] HALOALKYL ESTERS OF 5-NITROIMIDAZOLE-1-CARBOXYLIC ACID DERIVATIVES

[75] Inventors: Hans Nesvadba; Hellmuth Reinshagen, both of Vienna, Austria

[73] Assignee: Sandoz, Ltd., Basel, Switzerland

[22] Filed: Dec. 3, 1975

[21] Appl. No.: 637,312

[30] Foreign Application Priority Data

Dec. 6, 1974 Switzerland ............... 16233/74

[52] U.S. Cl. .................. 424/273; 260/240 A; 260/309
[51] Int. Cl.[2] ...................... C07D 233/94
[58] Field of Search ............ 260/309, 240 A; 424/273

[56] References Cited

UNITED STATES PATENTS

| | | | |
|---|---|---|---|
| 3,236,856 | 2/1966 | Parnell | 260/309 |
| 3,679,698 | 7/1972 | Beaman et al. | 260/309 |
| 3,952,007 | 4/1976 | Rufer et al. | 260/309 |

FOREIGN PATENTS OR APPLICATIONS

| | | | |
|---|---|---|---|
| 2,193,022 | 2/1974 | France | 260/309 |
| 509,382 | 8/1971 | Switzerland | 260/309 |

OTHER PUBLICATIONS

Blazevic et al., Chem. Abst. 1972, vol. 76, No. 113090s.

Aleshina et al., Chem. Abst. 1973, vol. 78, No. 111318q.
Henry, Chem. Abst. 1972, vol. 77, No. 5461a.
May & Baker Ltd., Chem. Abst. 1965, vol. 62, columns 9144–9145.

Primary Examiner—Natalie Trousof
Attorney, Agent, or Firm—Gerald D. Sharkin; Robert S. Honor; Thomas O. McGovern

[57] ABSTRACT

This invention provides compounds of the formula,

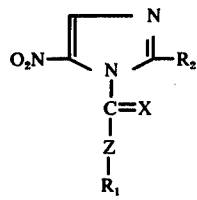

in which $R_1$ signifies straight or branched chain alkyl in which a single methyl group is replaced by a mono-, di- or tri-halomethyl group; $R_2$ signifies hydrogen or straight or branched chain lower alkyl and X and Z each independently signifies oxygen or sulphur, which are useful as animal feed additives and amoebicidal agents.

20 Claims, No Drawings

HALOALKYL ESTERS OF 5-NITROIMIDAZOLE-1-CARBOXYLIC ACID DERIVATIVES

This invention relates to 5-nitroimidazole derivatives.

More particularly, this invention provides compounds of formula I,

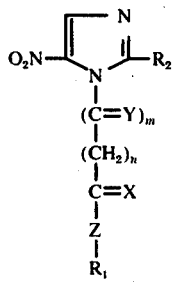

in which
- $R_1$ signifies straight or branched chain alkyl or alkenyl, unsubstituted, monosubstituted by phenyl or in which a single methyl group is replaced by a mono-, di or tri-halomethyl group; phenyl, unsubstituted or mono- or polysubstituted by nitro, lower alkyl or alkoxy, halogen or trifluoromethyl; or adamantyl,
- $R_2$ signifies hydrogen or straight or branched chain lower alkyl,
- X, Y and Z, which may be the same or different, each signifies oxygen or sulphur,
- $n$ signifies 0, 1, 2, 3 or 4, and
- $m$ signifies 0 or 1, provided that when $m$ is 0, X and Z each signifies oxygen, $n$ is 1 to 4 and $R_2$ is hydrogen or methyl, then $R_1$ is other than benzyl or unsubstituted alkyl or phenyl.

As used herein the term "lower" in connection with alkyl or alkoxy radicals, means containing, for example, 1 to 4 carbon atoms, in particular 1 to 2, more particularly 1 carbon atom. The term "halogen" means chlorine, bromine, fluorine or iodine, preferably chlorine or bromine.

Representative compounds of formula I include those of formula Ia,

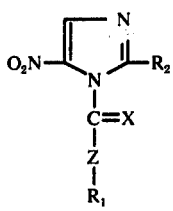

in which $R_1$, $R_2$, X and Z are as defined above.

The preferred compounds of formula Ia are those in which X and Z each signifies oxygen; X signifies oxygen and Z signifies sulphur; or X signifies sulphur and Z signifies oxygen.

Further representative compounds of formula I include those of formula Ib,

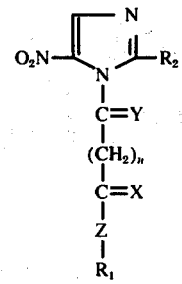

in which $R_1$, $R_2$, X, Y, Z and $n$ are as defined above, in particular those in which X, Y and Z each signify oxygen. In the compounds of formula Ib, $n$ preferably signifies 1 to 4, more preferably 2 to 4, in particular 2.

When $R_1$ represents a phenyl radical, such radical may, as indicated, be mono- or poly-substituted by the indicated substituents although, as will be appreciated by those skilled in the art, certain combinations of substituents may be ruled out by steric considerations. Preferably such phenyl radical is unsubstituted or substituted by one or two substituents, more preferably unsubstituted, or mono substituted, preferably by halogen, in particular by chlorine.

$R_1$ preferably signifies, however, an alkyl radical, particularly a straight chain alkyl radical, suitably containing 1 to 12, preferably 1 to 6, in particular 1 to 2 carbon atoms, or an alkenyl radical, preferably a straight chain alkenyl radical, suitably containing 2 to 6, preferably 2 to 4, in particular 3 carbon atoms. Such radicals may be unsubstituted or substituted as indicated, but are preferably unsubstituted or contain a mono-, di- or, preferably, tri-halomethyl group, in place of a single methyl group.

More preferably, $R_1$ signifies unsubstituted straight chain alkyl of 1 to 6 carbon atoms, particularly methyl or ethyl, unsubstituted straight chain alkenyl of 2 to 4 carbon atoms, particularly allyl, or $\omega$-$\omega$-$\omega$-tri-halo (particularly tri-chloro-)straight chain alkyl of 1 to 6, preferably 1 to 2 carbon atoms, in particular 2,2,2-trichloroethyl.

$R_2$ preferably signifies hydrogen or methyl.

The invention also provides a process for the production of compounds of formula I comprising reacting a compound of formula II,

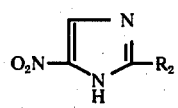

in which $R_2$ is as defined above, with a compound of formula III,

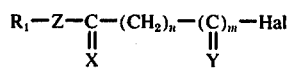

in which $R_1$, X, Y, Z, $m$ and $n$ are as defined above, and Hal signifies halogen.

The reaction is suitably effected in conventional manner, for example in an inert organic solvent, for example an aromatic hydrocarbon, such as benzene or toluene, and, conveniently, at an elevated temperature, for example at the reflux temperature of the reaction medium.

The resulting compounds of formula I may be isolated and purified using conventional techniques.

The compounds of formula III are either known or may be produced in known manner from available materials, for example by reacting a compound of formula IV,

in which $R_1$ and Z are as defined above, with a compound of formula V,

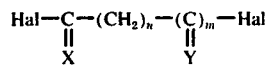

in which X, Y, n and m are as defined above, and both "Hal"s signify the same halogen atom.

The compounds of formula I possess nutritive activity and improve food utilisation, particularly in ruminants, in relatively low concentrations, and are therefore useful as animal feed additives, as indicated in vivo by addition of the compounds to animal feed, and in vitro with the aid of an artificial rumen. In this method, substances may be tested for their inhibition of methanogenese and/or their displacement of fatty acid formation in favour of propionate formation. Rumen juice is taken from the rumen of a ruminant and is filtered through gauze at 39° C while $CO_2$ is steadily bubbled through. The juice is then incubated together with the food used by the animal, which contains the test substance. After incubation, two samples are taken from the gas volume and tested, by gas chromatography, for methane and carbon dioxide. Finally, the liquid phase is tested for fatty acid content. Comparison with a sample not containing the test substance, gives an activity parameter. For example, a small amount, in particular 200 p.p.m. of the compounds of formula I may already reduce methane production by up to 95%. At comparable fermentation rates, the propionic acid production increases, particularly at higher concentrations of the compounds of formula I.

The compounds of formula I are therefore useful as animal feed additives. The concentration of additive in the animal feed will of course vary, for example depending on the compound employed. However, in general, satisfactory results are obtained when the compound of formula I is present in the feed at a concentration of 0.1 to 100 mg per kg of foodstuff.

For this use, i.e. as a nutritional aid, the compounds of formula I may also be administered in other ways, for example as tablets, boluses or capsules, or in drinking water. Such dosage forms may be produced in conventional manner. The dosage to be administered in such manner will be dependent on food consumption and can be calculated from the concentration range mentioned above.

The compounds of formula I also possess amoebicidal activity and are therefore useful as amoebicidal agents, as indicated in vitro in the series dilution test involving determination of the minimum lethal concentration of test substance after, for example, 48 hours cultivation at 37° C. The amoebicidal activity is determined, for example, in a TTY-SB medium against monoxenically cultivated E. histolytica amoeba (Diamond L.S., J. Parasit. 54, 715-719, [1968]) and at concentrations of, for example, 3.1 to 50 μg/ml. The activity is also confirmed in vivo in rats and hamsters, the criterium for activity being negative evidence of parasites in the animals which are treated perorally three times after infection with a daily dosage of, for example, 100 mg/kg of the compound of formula I.

For use in the treatment of amoebiasis, the dosage to be administered will of course vary depending on known factors, in particular the mode of administration and the particular compound employed. However, in general, satisfactory results are obtained when administered at a daily dosage of from about 30 to 300 mg/kg of animal body weight suitable given in divided doses 2 to 4 times daily, or in sustained release form. For the larger mammals, a suitable daily dosage is from about 2 to 5 g, and dosage forms suitable for oral administration, for example capsules or tablets, suitable comprise about 500 mg to 2.5 g of the compound in admixture with a solid or liquid pharmaceutical carrier or diluent.

The most preferred compounds of formula I include 2-methyl-5-nitroimidazole-1-carboxylic acid 2,2,2-trichloroethyl ester and 5-nitroimidazole-1-carboxylic acid 2,2,2-trichloroethyl ester.

The following Examples, in which all temperatures are in degrees Centigrade, illustrate the invention.

EXAMPLE 1

2-Methyl-5-nitroimidazole-1-carboxylic acid benzyl ester

A mixture of 10 g of 2-methhyl-5-nitroimidazole with 100 ml of a 50% solution of benzyl chloroformate in toluene is refluxed for 3 hours. After slowly cooling, the mixture is filtered to remove unreacted starting material and the filtrate is evaporated in vacuo. The residue is shaken with petroleum ether (b.p. 40°-60°) and the resulting crystals are filtered off and recrystallised from ethanol to yield the heading compound, m.p. 110°-111°.

In manner analogous to Example 1, and employing appropriate starting materials in approximately equivalent amounts, the following compounds may be obtained:

2. 2-methyl-5-nitroimidazole-1-carboxylic acid ethyl ester, b.p. $10^{-3}$ 110°;
3. 2-methyl-5-nitroimidazole-1-carbothioic acid O-phenyl ester, m.p. 106°-109°.
4. 2-methyl-5-nitromidazole-1-carboxylic acid allyl ester, m.p. 61°-64°;
5. 2-methyl-5-nitroimidazole-1-carboxylic acid 2,2,2-trichloroethyl ester, m.p. 86°-88°;
6. 2-methyl-5-nitro-imidazole-1-carbothioic acid S-ethyl ester, b.p. $10^{-3}$ 125°;
7. 2-methyl-5-nitroimidazole-1-carbothioic acid 0-(4-chlorophenyl)ester, m.p. 102°-104°;
8. 5-nitroimidazole-1-carboxylic acid ethyl ester, m.p. 58°-59°;
9. 5-nitroimidazole-1-carboxylic acid allyl ester, m.p. 51°-53°;
10. 4-(2-methyl-5-nitro-1-imidazolyl)-4-oxobutyric acid methyl ester, m.p. 101°-104°;
11. 4-(5-nitro-1-imidazolyl)-4-oxobutyric acid methyl ester, m.p. 64°-66°;
12. 5-nitroimidazolyl-1-carboxylic acid 2,2,2-trichloroethyl ester, 102°-104°;
13. 2-methyl-5-nitroimidazole-1-carbothioic acid S-(1-adamantyl)ester, m.p. 163°-167°;

14. 2-methyl-5-nitroimidazole-1-carboxylic acid methyl ester;
15. 2-methyl-5-nitroimidazole-1-carboxylic acid phenyl ester;
16. 2-methyl-5-nitroimidazole-1-carboxylic acid 6-chlorohexyl ester;
17. 2-methyl-5-nitroimidazole-1-carboxylic acid 4,4-dibromobutyl ester;
18. 2-methyl-5-nitroimidazole-1-carboxylic-p-chlorophenyl ester.
19. 2-methyl-5-nitroimidazole-1-carbothioic acid S-methyl ester;
20. 2-methyl-5-nitroimidazole-1-carbothioic acid 0-(2-bromoethyl)ester; 21. 2-methyl-5-nitroimidazole-1-carbothioic acid S-allyl ester.
22. 2-methyl-5-nitroimidazole-1-carbothioic acid 0-(6,6,6-trichlorohexyl)ester;
23. 2-methyl-5-nitroimidazole-1-carbothioic acid 0-(2,2-dichloroethyl)ester;
24. 4-(2-methyl-5-nitro-1-imidazolyl)-4-oxobutyric acid hexyl ester;
25. 4-(5-nitro-1-imidazolyl)-4-oxobutyric acid allyl ester;
26. 4-(2-methyl-5-nitro-1-imidazolyl)-4-oxobutyric acid(2-chloroethyl)ester;
27. 4-(2-methyl-5-nitro-1-imidazolyl)-4-oxobutyric acid (6,6,6-trichlorohexyl)ester;
28. 4-(5-nitro-1-imidazolyl)-4-oxobutyric acid trichloromethyl ester;
29. 3-(2-methyl-5-nitro-1-imidazolyl)-3-oxopropionic acid phenyl ester;
30. 5-(5-nitro-1-imidazolyl)-5-oxopentanoic acid 1-admantyl ester;
31. 6-(2-methyl-5-nitro-1-imidazolyl)-6-oxohexanoic acid 2-bromoethyl ester

What is claimed is:

1. A compound of the formula,

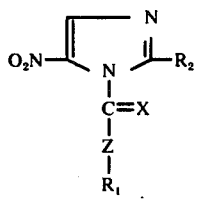

in which
$R_1$ signifies straight or branched chain alkyl of 1 to 12 carbon atoms which contains a mono-, di- or tri-halomethyl group in place of a methyl group in the alkyl chain.
$R_2$ signifies hydrogen or straight or branched chain lower alkyl of 1 to 4 carbon atoms and
X and Z, which may be the same or different, each signifies oxygen or sulphur.

2. A compound of claim 1 in which $R_1$ is alkyl or 1 to 6 carbon atoms in which a methyl group is replaced by a mono-, di- or tri-halomethyl group.

3. A compound of claim 2, in which $R_1$ is straight chain alkyl of 1 to 6 carbon atoms in which a methyl group is replaced by a mono-, di- or tri-halomethyl group.

4. A compound of claim 1 in which $R_1$ is ω, ω, ω-triahalo-straight chain alkyl of 1 to 6 carbon atoms.

5. Compounds of claim 1, in which $R_1$ is 2,2,2-trichloroethyl.

6. The compound of claim 1, which is 2-methyl-5-nitroimidazole-1-carboxylic acid 2,2,2-trichloroethyl ester.

7. The compound of claim 1, which is 5-nitroimidazole-1-carboxylic acid 2,2,2-trichloroethyl ester.

8. The compound of claim 1 which is 2-methyl-5-nitroimidazole-1-carboxylic acid 6-chlorohexyl ester.

9. The compound of claim 1 which is 2-methyl-5-nitroimidazole-1-carboxylic acid 4,4-dibromobutyl ester.

10. The compound of claim 1 which is 2-methyl-5-nitroimidazole-1-carbothioic acid 0-(2-bromoethyl)ester.

11. The compound of claim 1 which is 2-methyl-5-nitroimidazole-1-carbothioic acid 0-(6,6,6-trichlorohexyl)ester.

12. The compound of claim 1 which is 2-methyl-5-nitroimidazole-1-carbothioic acid 0-(2,2-dichloroethyl)ester.

13. The compound of claim 1 which is 4-(2-methyl-5-nitro-1-imidazolyl)-4-oxobutyric acid (2-chloroethyl)ester.

14. The compound of claim 1 which is 4-(2-methyl-5-nitro-1-imidazolyl)-4-oxobutyric acid (6,6,6-trichlorohexyl)ester.

15. The compound of claim 1 which is 4-(5-nitro-1-imidazolyl)-4-oxobutyric acid trichloromethyl ester.

16. The compound of claim 1 which is 6-(2-methyl-5-nitro-1-imidazolyl)-6-oxohexanoic acid 2-bromoethyl ester.

17. A method of improving animal food utilisation comprising administering an effective amount of a compound of claim 1.

18. A method of improving animal food utilisation comprising administering a effective amount of a compound of claim 1 in admixture with the animal feed.

19. An animal feed comprising a compound of claim 1 in an amount effective to improve food utilisation.

20. A method of treating amoebiasis comprising administering to an animal in need of such treatment an amoebicidally effectively amount of a compound of claim 1.

* * * * *